(12) United States Patent
Bullivant et al.

(10) Patent No.: US 6,440,140 B2
(45) Date of Patent: Aug. 27, 2002

(54) ANCILLARY APPARATUS FOR KNEE PROSTHESIS

(75) Inventors: Mike Bullivant, Doncaster (GB); Alberto Siccardi, Villa Luganese (CH)

(73) Assignee: Medacta S.A., Luxembourg (LU)

( * ) Notice: Subject to any disclaimer, the term of this patent is extended or adjusted under 35 U.S.C. 154(b) by 0 days.

(21) Appl. No.: 09/773,645

(22) Filed: Jan. 31, 2001

(51) Int. Cl.$^7$ ............................................... A61B 17/58
(52) U.S. Cl. ........................... 606/89; 606/88; 606/82; 606/86
(58) Field of Search ..................... 606/88, 87, 86, 606/66, 59, 82, 89, 53, 76

(56) References Cited

U.S. PATENT DOCUMENTS 5,749,876 A * 5/1998 Duvillier .................... 606/88
5,925,049 A * 7/1999 Gustilo et al. ............... 606/88
6,007,537 A * 12/1999 Burkinshaw et al. ......... 606/88
6,102,916 A * 8/2000 Masini ....................... 606/88

FOREIGN PATENT DOCUMENTS

FR                 538153        *  4/1993   ................. 606/88

* cited by examiner

Primary Examiner—Pedro Philogene
(74) Attorney, Agent, or Firm—Ostrolenk, Faber, Gerb & Soffen, LLP

(57) ABSTRACT

Apparatus to guide blades or saws of femoral cuts for knee prosthesis, consisting of four blocks, two blocks which move only vertically and two blocks which move only horizontally. Cams are provided which are accompanied by followers and have helix tracks whose pitch permits the apparatus to adapt to different prostheses.

7 Claims, 7 Drawing Sheets

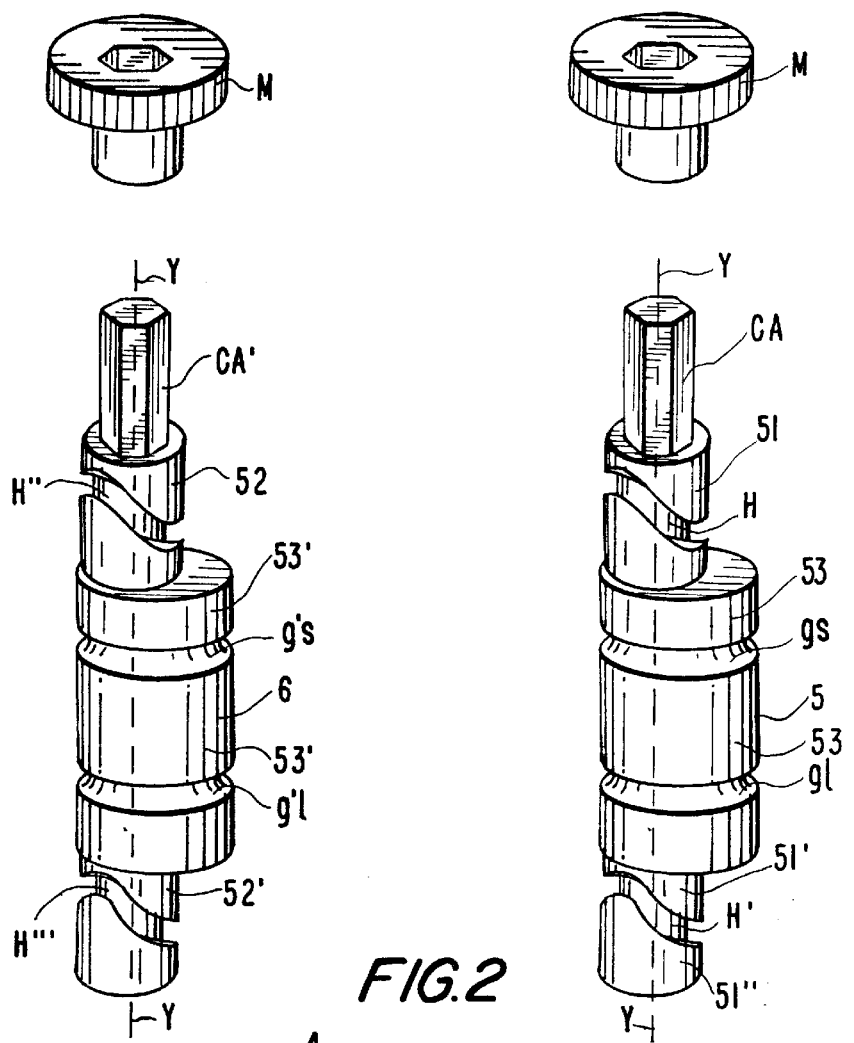
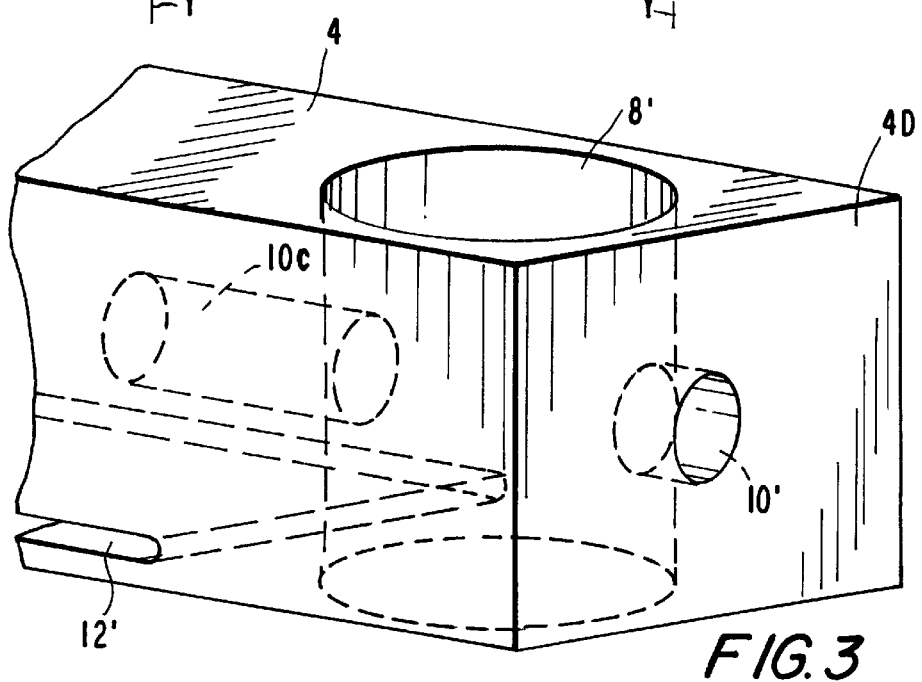
FIG.2
FIG.3

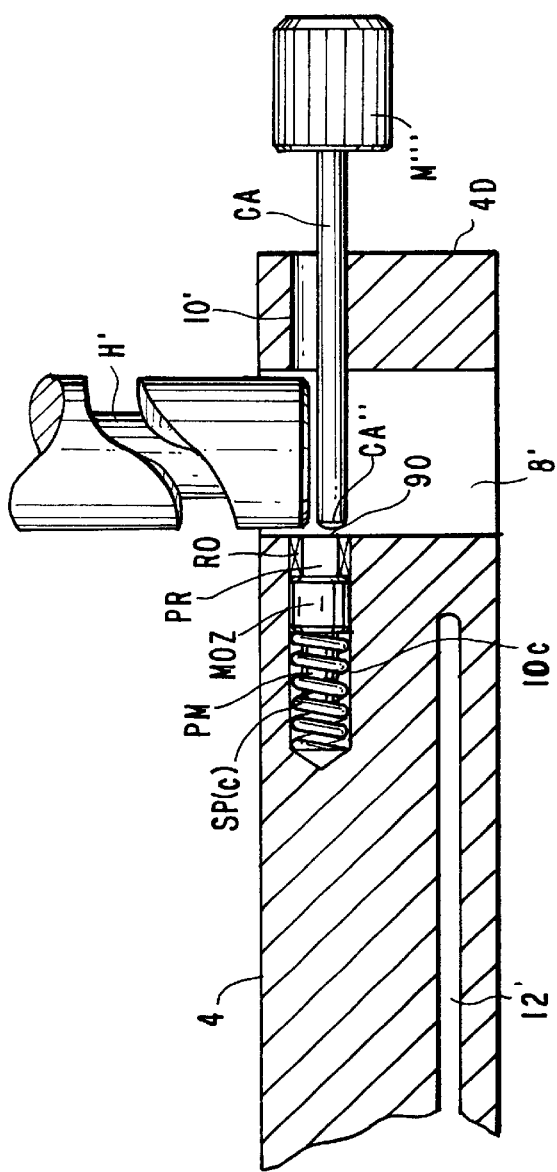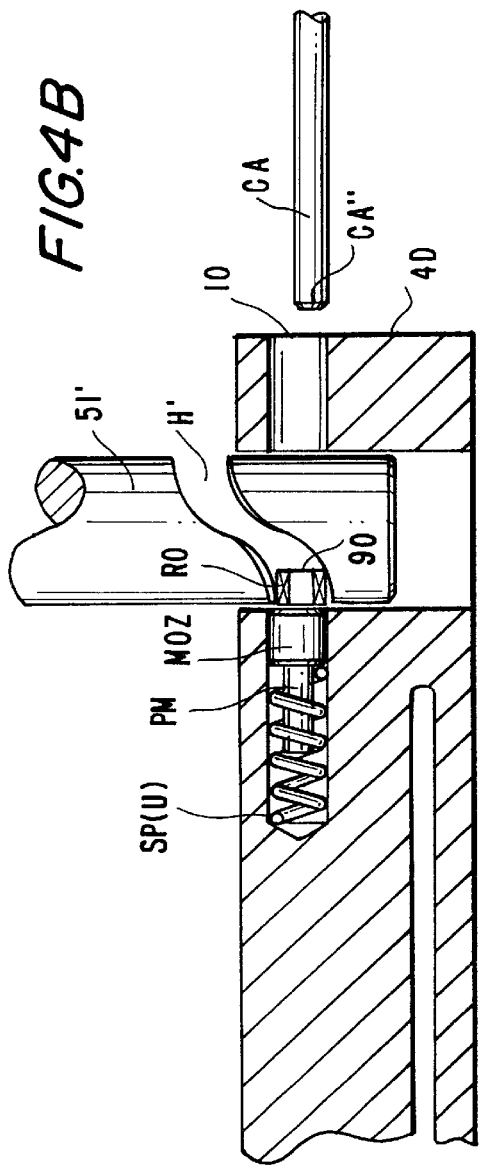

US 6,440,140 B2

ANCILLARY APPARATUS FOR KNEE PROSTHESIS

BACKGROUND OF THE INVENTION

The present invention concerns an ancillary apparatus for knee prosthesis.

It is known that knee breaks and/or diseases particularly arthritic diseases are becoming today more frequent, above all, in the increasing sport activities field as in the non-sport practicing population because of age or life lengthening and/or simply greater mobility.

The instruments for knee interventions have seen an enormous expansion and innumerable are the proposals and structures suggested in the literature or applied in hospital practice also, and mainly in the attempt to suggest and finally provide an apparatus of universal character, i.e., able to be applied to the knee in different forms and sizes which knowingly vary from one person to the other.

Among the numerous patents and patent publications, may be mentioned U.S. Pat. Nos. 4,892,093, 5,474,559, 5,749,876, European Patent Publications No. 0538,152, No. 0538,153, No. 0555,003, and French Patents No. 2,664,157, No. 2,679,766, No. 2,629,339, No. 2,681,779.

French Patent No. 2,679,766 discloses a femoral cut device for the correct positioning of prosthesis implants in the femoral and sagittal planes, which however needs several guides of cutting blades of different sizes for prosthesis to adapt to the different articulation sizes: some risks in the correct guide positioning are possible.

The resection apparatus according to French Patent No. 2,664,157 includes a guide for the cutting blades in two blocks, one movable with the bevelling cuts support and one adjustable in height for the anterior cut.

In the PCT-Publication WO96/01588 (corresponding to U.S. Pat. No. 5,749,876 and EP No. 0721314) the apparatus for the knee condyles resection and for the positioning of a prosthesis comprises: a support with an inferior basis; a guide of the blades of the anterior and posterior cuts, either chamfer or not; an intramedullary femoral rod, and tracer or contact means, said guide having three blocks two of which are mobile and adjustable in height; further one of the blocks comprises means to guide one of the anterior, posterior chamfer (or not) cuts, and the other two blocks comprise guide means for the remaining cuts.

There is no doubt that the proposed solutions and devices, above all those according to said U.S. Pat. No. 5,749,876, have merit, however, they are never free of structural complexities which, moreover, involve operative complications; further they have production and running costs which strongly handicap a generalized diffusion.

The first object of the present invention is to provide an instrumentation particularly simple, compact, reliable and universal both in structural and operative terms.

Another object of the invention is to provide adjustment and control means which are decidedly advantageous compared with the corresponding ones of the prior art.

SUMMARY OF THE INVENTION

The present invention concerns an ancillary apparatus for knee prosthesis, in particular for guiding the femoral cut blades or saws which permit the insertion of the prosthesis components mostly adapted to the conformation of each patient, said apparatus comprising several blade-guide blocks vertically approached, in this case a first inferior (lower or bottom) block (4) for posterior cut guide, a superior or head block for the anterior cut, two median (intermediate) blocks (2 and 3) for posterior (2), anterior (3) chamfer cuts, and means (5, 6) of support, seal and motion of said blocks.

According to a first feature of the invention the apparatus is characterized in that said anterior and superior (i.e., terminal) blocks are only vertically movable, have at least two vertical holes for the passage of motion means, at least one horizontal hole for the insertion of means complementary to said means and front slits which are inclined to a horizontal line, are remote in respect to the inferior and superior edges of said end blocks; the intermediate blocks move only horizontally, are provided with holes corresponding to the holes and inclined slits on the edges of said intermediate blocks.

BRIEF DESCRIPTION OF THE DRAWINGS

The various features and advantages of the invention will better appear from the following description of the (not-limitative) embodiments shown in the accompanying drawings in which:

FIG. 2 is a partially exploded perspective view of two motion cams;

FIG. 3 is a partially perspective and enlarged view of only the right portion 40 of block 4;

FIGS. 4A and 4B are the vertical cross-sections with a plane having the line A', A" as traced on said right portion 4D of block 4, FIG. 4A showing the uncompressed spring and FIG. 4B showing the compressed spring;

DETAILED DESCRIPTION OF THE PREFERRED EMBODIMENT

Figure 1:
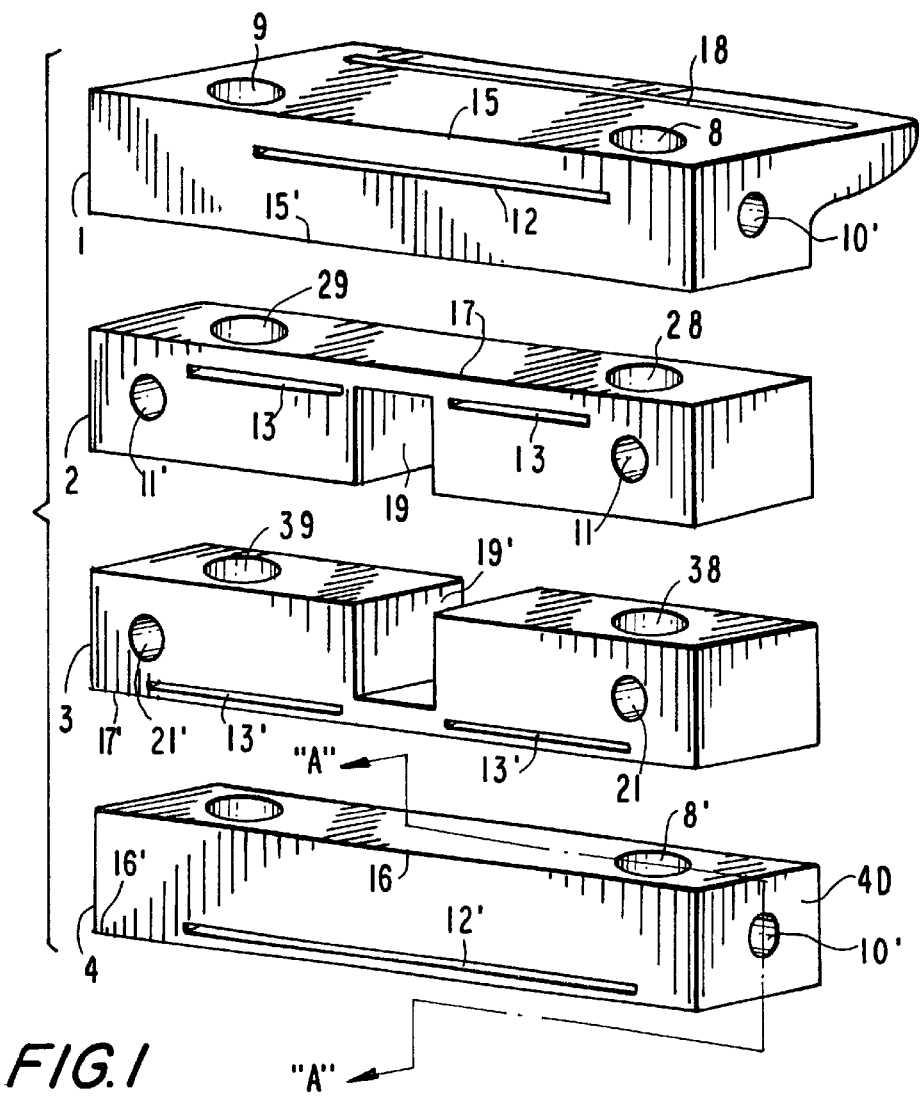
FIG. 1 is a perspective and partially exploded view of the four blocks in the instrumentation according to the invention.

FIG. 1 shows the four saw-guide blocks from 1 to 4 in exploded position, i.e. detached from each other. The end blocks namely the upper (superior) 1 and lower (inferior) 4 block, as well as the median blocks 2 and 3 show vertical hole couples 8–9, 8'–9', 28–29, 38–39, respectively, for the passage of the motion means 5 and 6 (FIG. 2).

The terminal blocks 1 and 4 are horizontal blocks 10–10' for the insertion of the means IA complementary to said means 5 and 6. In an advantageous and preferred embodiment of the invention, the motion means 5 and 6 are cams and the complementary means are cam followers.

The superior block 1 and the inferior block 4 show slanting slits 12, 12', respectively, for the anterior cut AC

(12) and posterior cut PC (12') (see FIG. 11), as well as horizontal holes 10, 10' for the insertion of the cam follower device IA.

Figure 11:
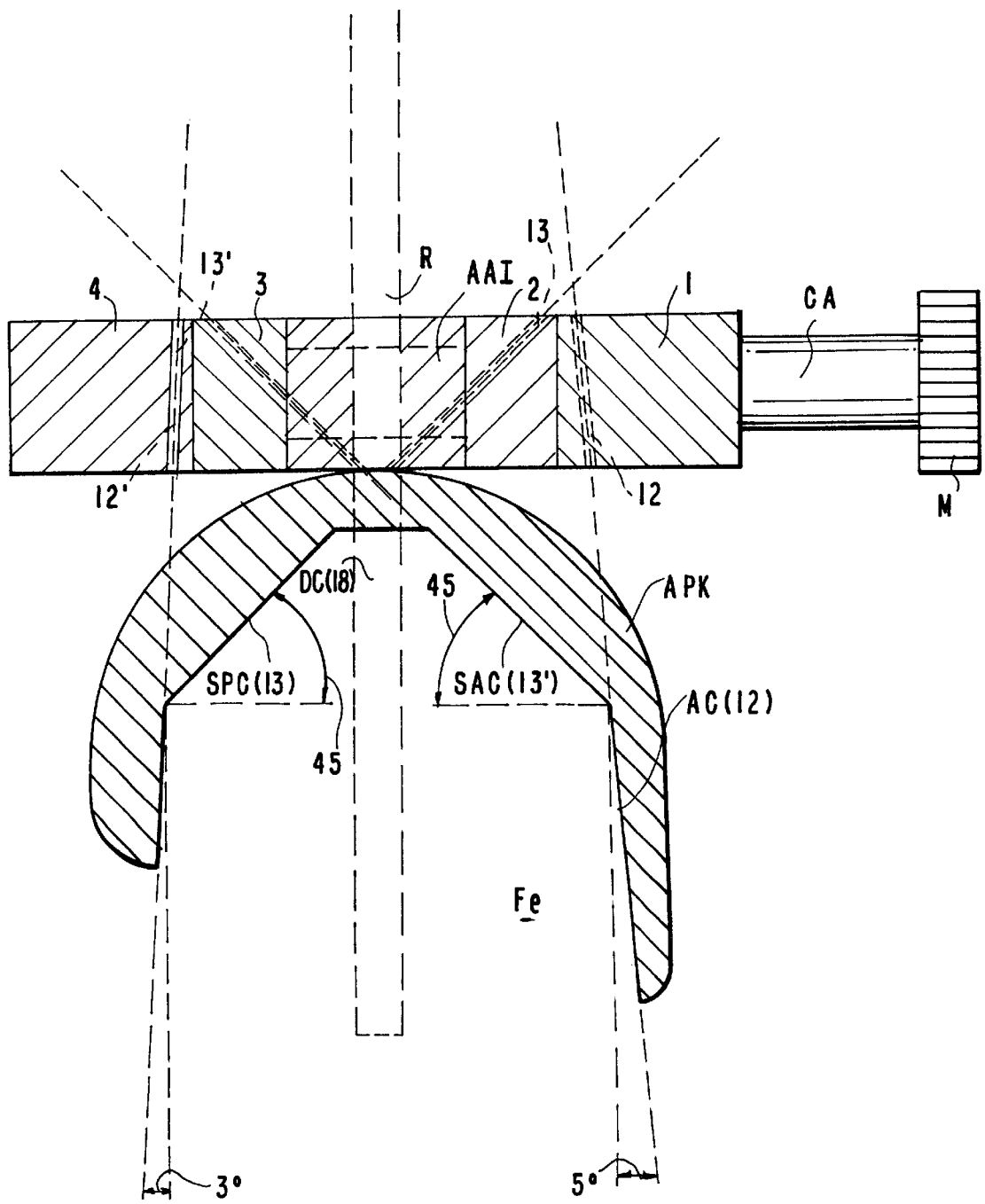
FIG. 11 is a schematic cross-section of the apparatus according to the invention, on a knee together with the five made cuts.

The head (superior) block 1 has additionally the slit 18 for the distal cut DC (18) in FIG. 11. The slits 12 and 12' are sufficiently remote in respect to the edges 15 and 16, respectively, whereas the slits 13 and 13' are preferably near the edges 17 and 17'. The median blocks 2 and 3 have facing recesses 19 and 19'.

According to a feature of the invention, the terminal blocks 1 and 4 are moved only vertically and median blocks 2 and 3 are moved only in a horizontal plane.

The motion means are of the cam type 5 and 6 and, typically, show on a nucleus or central axis CA two portions with a minor diameter 51–51', 52–52' in which are provided the helix tracks H–H', H"—H", as well as two portions with major diameter 53—53', 53"–53" in which are present the grooves Gs–G1, G's–G'1, respectively.

At the superior edge of CA, CA' are engaged the handles M, M'.

Figure 5:
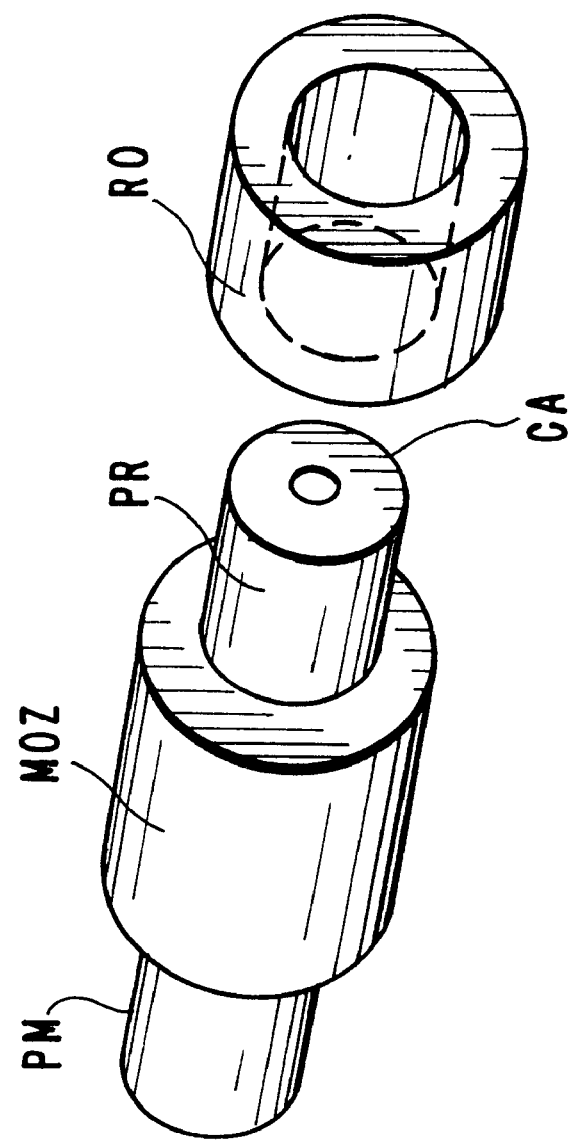
FIG. 5 is an exploded and perspective view of the cam follower.

In the perspective view of FIG. 3 is represented on an enlarged scale only the right portion 4D of block 4, in order to better show the horizontal hole 10' with its continuation 10C which will act as the cavity for the spring SP of the cam follower that is shown in exploded form in FIG. 5 and consists of a central hub or boss MOZ from which protrude two shafts PR and PM having a diameter lower than that of MOZ. On the pin PR is keyed roller RO which facilitates the rotation of the whole piece MOZ+PR+PM for horizontal displacement.

FIGS. 4A and 4B show block 4 with hole 10' in which penetrates the central shaft CA (see FIGS. 4A–4B and 5) extending up to the anterior face of roller RO mounted on pin PR of hub MOZ whose second pin PM acts on spring SP. Obviously the pieces MOZ+RO+PM+SO which form the follower IA of cam 5–6 have been previously inserted in cavity 10C which is on the continuation of shaft CA.

Once spring SP and means MOZ with roll RO have been inserted in the cavity 10C, the end CA" of shaft CA is pushed against the face 90 of roll RO through which MOZ compresses spring SP whereby we go from the configuration with relaxed spring SP (u) of FIG. 4B to the configuration with compressed spring SP(c) of FIG. 4A. Once said spring SP(c) is compressed, cam 5 is inserted in hole 8' till the end 51" of the inferior portion with minor diameter 51' is engaged with a part of roller RO face 90; with said engagement of roller RO (90) with the inferior portion 51", it is possible to re-extract the central shaft CA (pulling knob M'") because the inferior base 51" of the lower part 51' of cam 5 insisting on face 90 of roller RO keeps the spring compressed as in FIG. 4A.

Shaft CA can now be unthreaded and in the free portion so obtained the cam 5 is vertically pushed down till roller RO engages track H'. With this insertion of RO into H' the surgeon turns the handle M whereby roller RO re-ascends said track H' and translates along vertical axis Y—Y of cam 5 thereby vertically displacing block 4.

The same procedure takes place for the cam 5 superior portion 51, i.e., after that the cam has been taken in position of FIG. 4A, also the superior part 51 of 5 engages its follower IA housed in the cavity 10c of the superior block 1. Blocks from 1 to 4 can be seen compacted in FIG. 6, blocks 1 and 4 containing the superior followers IAs and IAs' being inserted in the hole 10' and 10'" of block 4.

Figure 6:
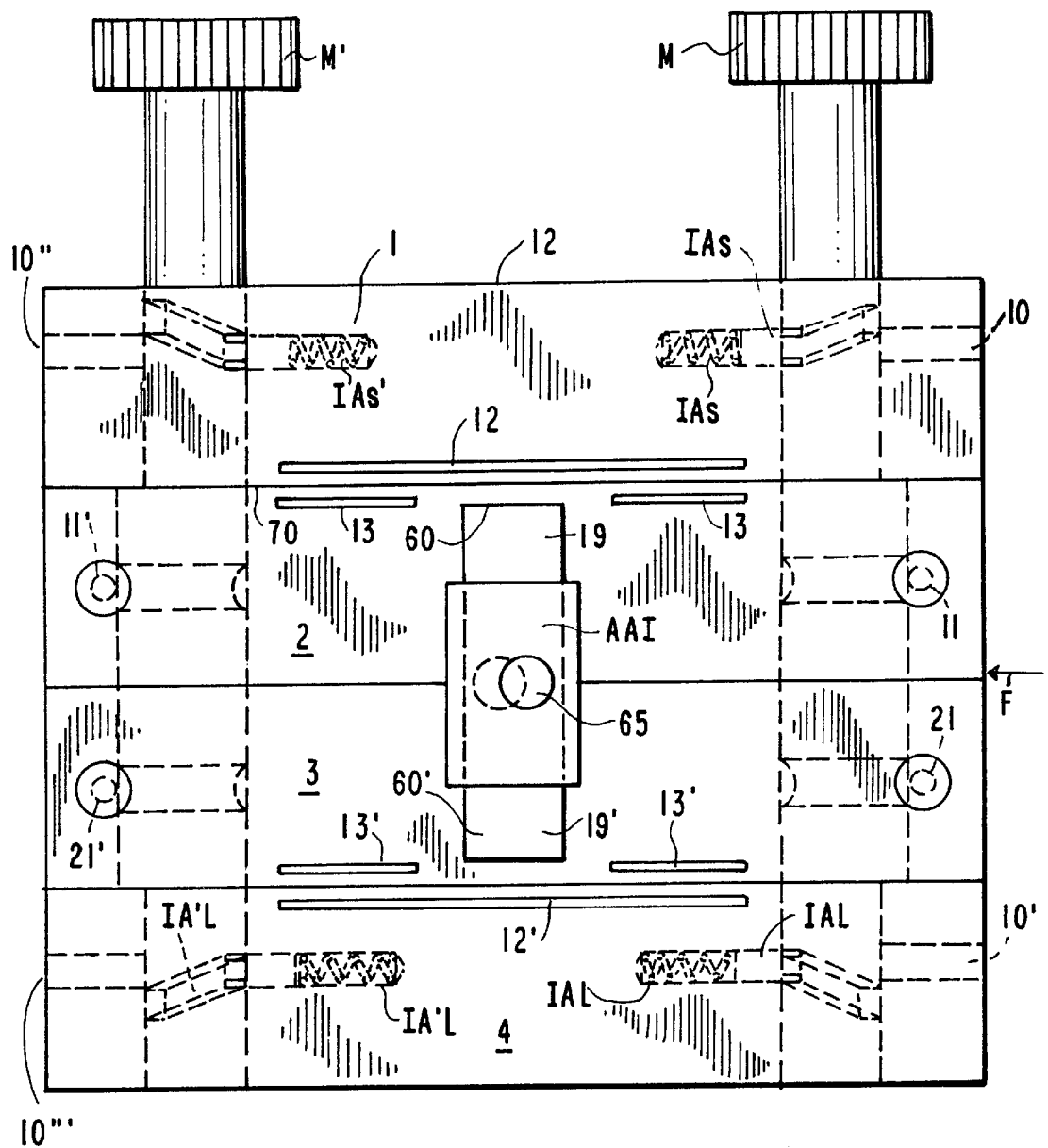
FIG. 6 is the front view of the four compacted blocks, with cams 5 and 6 inserted in all vertical holes and with the cam IA followers inserted in the two horizontal holes 10–10', and with the insert of the anatomic angle AAI fixation set in the two recesses 19–19' of the two median blocks.

In FIG. 6, reference AAI indicates the anatomical degree insert with the relevant hole 65 inserted in the recess 19 of block 2 and recess 19' of block 3. Overall, in FIG. 6 as well as in FIGS. 2 and 3, the slits 13 and 13' associated to the median block 2 and 3 are indicated as formed of two pieces. They can be formed of only one piece (monopiece) as 12 and 12' which, at the limit, can also consist of several pieces (multipieces).

In general, the rotation of handles M, M' of cams 5 and 6 amounts to a half revolution, i.e. 180°. Preferably it proceeds at determinated steps of the pawls and springs associated to M and M' (not shown because they are conventional).

Figure 7:
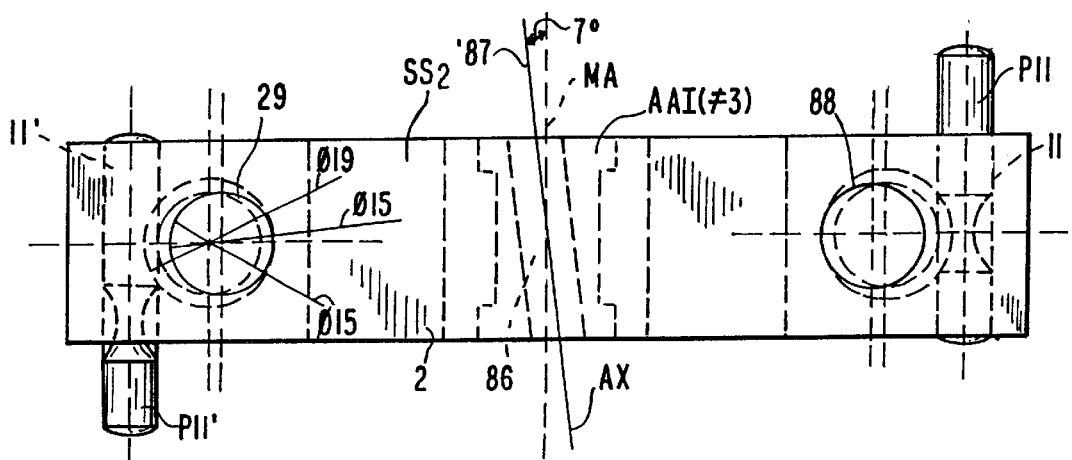
FIG. 7 is a top view of the flat face 7D of block 2.
Figure 8:
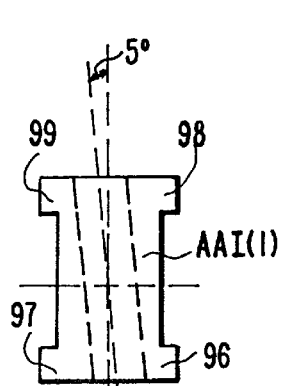
FIGS. 8 to 8D are top views of five embodiments of the anatomic angle AAI adjusting insert having an H form.
Figure 8A:
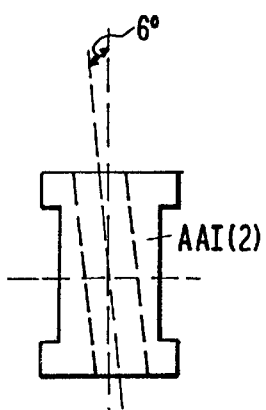
Figure 8B:
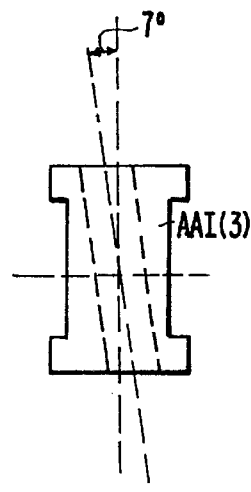
Figure 8C:
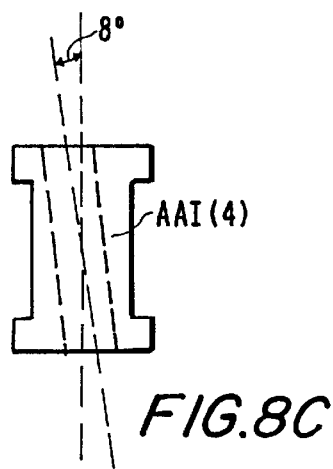
Figure 8D:
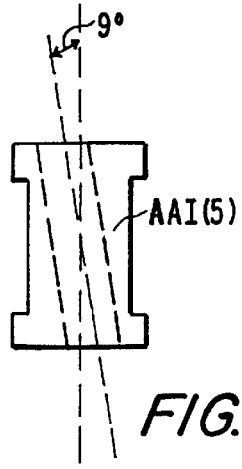

FIG. 7 is a top view of the top SS2 of block 2 and shows the dashed holes 11 and 11' in which are inserted the pins P11 and P11' which go in engagement in the superior grooves Gs and G's of the superior portions 53 and 53' of 5 and 6 (FIG. 2).

Similarly pins or plungers P21 and P21' (FIG. 10) will be inserted in holes 21–21" of blocks 3 and will engage inferior grooves G1 and G'1. These engagements of the four pins or plungers P11–P11' and P21–P'21 with the four grooves G's–G1—G's–G1 (FIG. 2) will inhibit vertical movement of the "ensemble" of the four assembled blocks 1–4.

The insert of anatomical angle AAI (FIG. 7) has a hole 86 whose median axis or central line 97 coincident with the anatomical axis AX has an inclination over the geometrical or mechanical axis MA, which can generally vary between 4° and 10° preferably between 5° and 9°. Therefore according to the patient anatomical axis AX the surgeon will select the insert AAI with the inclination adequate to the involved patient anatomical axis.

Figure 9:
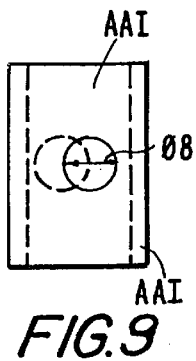
FIG. 9 is a front view of AAI.

The top views of FIGS. 8, 8A, 8B and 8C (similar to FIG. 7) show the five inserts from AAI (1) to AAI (5) with the inclinations from 5° to 9° capable to cover the case majority. FIG. 9 is a front view of a typical insert AAI, the insert from AAI (1) to AAI (5) being seen from the top.

Figure 10:
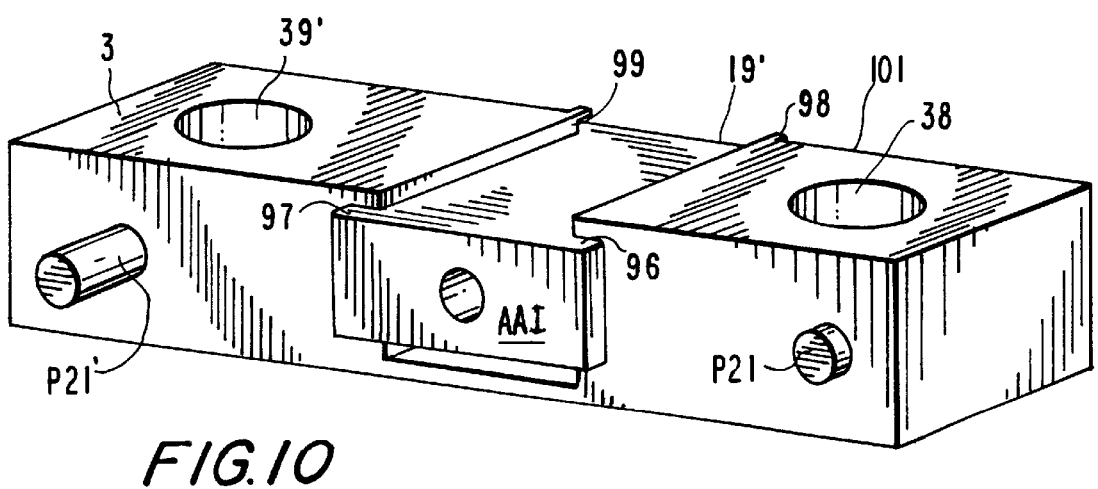
FIG. 10 is a perspective view of the insert AAI joint in the two recesses 19–19' worked in the two intermediate blocks 2 and 3.

FIG. 10 shows the partial perspective of a median block, in this case block 3 with the insert AAI entered in the recess 19'; to this end insert AAI has a H-shape with four protruberances 96–97 (forward, anterior) and 98–98' (rearward, posterior) which ledge or partially extend over the lateral faces 96–97 (anterior) and 98–99 (posterior) of block 3.

FIG. 11 is a side view (for example, according to arrow F of FIG. 6) of the assembly of blocks 1, 2, 3, and 4, each block being represented together with the inclined axis of its own slit 12, 12' (generally, inclination of about 3° or 5°) and 13, 13' (45° inclinations).

In the assembly center, namely through the control portion of block 2, goes (passes) rod R placed on the anatomical axis AX. APK indicates the anatomical profiles of femur Fe and the cuts made by the blades or saws guided by blocks 1–4 are indicated by references AC (12), anterior cut PC (12'), posterior cut, SAC (13') anterior chamfered cut, SPC 13 posterior chamfered cut, and DC (18) distal cut.

The assembling sequence of the apparatus according to the invention is: insertion of anatomical axis AX in block 3; insertion of cams 5 and 6 within said block 3; insertion of pins P12 and P'12 in the holes 21 and 21' of block 3; engagement of the major diameter portions 53' and 53" in the holes 28–29 of block 2; engagement of pins P11 and P' 11 into holes 11 and 11' to assure the assembly seal; insertion into the holes 10' and 10" of block 4 of cam followers, namely of spring SP and hub MOZ together with roll RO; compression of said spring, withdrawing of shaft CA and insertion of the threaded portions 51'–51" and 52–52" up to the click or release engagement with the relevant rollers; and repetition of the engagement of the helixes H and H" with the respective rollers.

The hospital attendants will have no difficulty in carrying out this assembly whereas the surgeon must substantially limit himself to maneuver the handles M and M' which, because of the helix profiles in the portions 51 and 51' of the cams, and of the eccentricity of the major diameter portions 53, 53' respectively (i.e. in respect of 51 and 51') provide the vertical movements of blocks 2 and 3 in relation to blocks 1 and 4.

For illustrative clarity, the invention has been described with particular reference to the embodiments represented in the accompanying drawings. It is obvious that all the changes, alternatives, substitutions and the like to said embodiments which are in the reach of one skilled in the art, and are to be considered as falling within the scope and spirit of the following claims.

What is claimed is:

1. An ancillary apparatus for knee prosthesis, in particular for guiding the femoral cut blades or saws which permit the insertion of the prosthesis components mostly adapted to the conformation of each patient, said apparatus comprising several blade-guide blocks vertically approached, including a first inferior, (lower or bottom) block for posterior cut guide, a superior (head) block for the anterior cut, two median blocks for posterior, anterior chamfer cuts, and means of support, seal and motion of said blocks taken singularly and/or all together, characterized in that said terminal blocks are only vertically movable, have at least two vertical holes for the passage of said motion means, at least one horizontal hole for the insertion of means complementary to said means front slits which are inclined on a horizontal line, are remote in respect to the inferior and superior edges of said end blocks; and a top slit the intermediate blocks being moveable only horizontally, being provided with holes corresponding to said holes and with inclined slits on the edges respectively of said intermediate blocks.

2. Apparatus according to claim 1, characterized in that the motion means are cams comprising two terminal portions, two intermediate portions and two intermediate portions with diameter diversity, the two extreme portions with minor diameter being provided with spiral or helix tracks, the intermediate portions with major diameter being, each, provided with at least a groove.

3. Apparatus according to claim 2, characterized in that the two intermediate portions with major diameter are eccentric in respect to said two extreme portions.

4. Apparatus according to claim 1, characterized by being adaptable to femur components of different design and size, by varying the helix or spiral pitch on the extreme portions with minor diameter of the cam guides.

5. Apparatus according to claim 4, characterized in that said adaptability is enhanced by playing also on the position of said slits in said blocks.

6. Apparatus according to claim 2, characterized in that the means cooperating with said cams include a hub or boss and a spring.

7. Apparatus according to claim 6, wherein said hub or boss includes a central body having a major diameter from which minor diameter pins protrude, on one of which is keyed a roller whereas the free end of the other pin insists on the spring.

\* \* \* \* \*